US012624371B2

(12) United States Patent
Liu et al.

(10) Patent No.: US 12,624,371 B2
(45) Date of Patent: May 12, 2026

(54) PROCESS TO TREAT A CARBON DIOXIDE COMPRISING GAS

(71) Applicant: PAQELL B.V., Utrecht (NL)

(72) Inventors: Dandan Liu, Wageningen (NL);
Frederikus De Rink, Amersfoot (NL);
Johannes Bernardus Maria Klok,
Rhenen (NL)

(73) Assignee: PAQELL B.V., Utrecht (NL)

( * ) Notice: Subject to any disclaimer, the term of this patent is extended or adjusted under 35 U.S.C. 154(b) by 406 days.

(21) Appl. No.: 18/028,860

(22) PCT Filed: Oct. 13, 2021

(86) PCT No.: PCT/EP2021/078266
§ 371 (c)(1),
(2) Date: Mar. 28, 2023

(87) PCT Pub. No.: WO2022/079081
PCT Pub. Date: Apr. 21, 2022

(65) Prior Publication Data
US 2023/0287462 A1 Sep. 14, 2023

(30) Foreign Application Priority Data

Oct. 13, 2020 (NL) ..................................... 2026669

(51) Int. Cl.
| | |
|---|---|
| *C12P 5/02* | (2006.01) |
| *C12M 1/107* | (2006.01) |
| *C12M 1/12* | (2006.01) |
| *C12M 1/42* | (2006.01) |
| *C25B 3/03* | (2021.01) |
| *C25B 3/26* | (2021.01) |
| *C25B 9/40* | (2021.01) |
| *C25B 11/063* | (2021.01) |
| *C25B 11/065* | (2021.01) |
| *C25B 11/075* | (2021.01) |
| *C25B 15/08* | (2006.01) |

(52) U.S. Cl.
CPC ............. *C12P 5/023* (2013.01); *C12M 21/04* (2013.01); *C12M 25/18* (2013.01); *C12M 35/02* (2013.01); *C25B 3/03* (2021.01); *C25B*
*3/26* (2021.01); *C25B 9/47* (2021.01); *C25B 11/063* (2021.01); *C25B 11/065* (2021.01); *C25B 11/075* (2021.01); *C25B 15/083* (2021.01)

(58) Field of Classification Search
CPC ....................................................... C12P 5/023
See application file for complete search history.

(56) References Cited

U.S. PATENT DOCUMENTS

2009/0317882 A1 12/2009 Shaoan et al.

FOREIGN PATENT DOCUMENTS

| CN | 106947688 B | 3/2019 |
|---|---|---|
| CN | 110284150 A | 9/2019 |
| WO | 2011/003081 A1 | 1/2011 |
| WO | 2014/016815 A2 | 1/2014 |

OTHER PUBLICATIONS

U.S. Appl. No. 18/712,073 (Year: 2024).*
Liu et al., "Granular Carbon-Based Electrodes as Cathodes in Methane-Producing Bioelectrochemical Systems", Frontiers in Bioengineering and Biotechnology, vol. 6(78), pp. 1-10 (Jun. 12, 2018).
Liu et al., "Supporting Information for the article: Granular Carbon-Based Electrodes as Cathodes in Methane-Producing Bioelectrochemical Systems", Frontiers in Bioengineering and Biotechnology, vol. 6(78), 12 pages Jun. 12, 2018).
Zeppilli et al., "Anion VS cation exchange membrane strongly affect mechanisms and yield of CO2 fixation in a microbial electrolysis cell", Chemical Engeneering Journal, Elsevier, Amsterdam, NL, vol. 304, (Jun. 4, 2016), pp. 10-19.

* cited by examiner

*Primary Examiner* — Ruth A Davis
(74) *Attorney, Agent, or Firm* — NIXON PEABODY LLP; Ronald I. Eisenstein; Nicole D. Kling

(57) ABSTRACT

The invention is directed to a process to convert carbon dioxide to methane by contacting an aqueous solution comprising dissolved carbon dioxide with an electron charged packed bed comprising of a carrier, suitably activated carbon granules, and a biofilm of microorganisms under anaerobic conditions, wherein more than 90 mol % of the dissolved carbon dioxide in the aqueous solution is present as a bicarbonate ion and/or as a carbonate ion.

19 Claims, 2 Drawing Sheets

PROCESS TO TREAT A CARBON DIOXIDE COMPRISING GAS

CROSS-REFERENCE TO RELATED APPLICATIONS

This application is a 35 U.S.C. § 371 National Phase Entry Application of International Application No. PCT/EP2021/078266 filed Oct. 13, 2021, which designates the U.S. and claims benefit under 35 U.S.C. § 119(a) of NL Application No. 2026669 filed Oct. 13, 2020, the contents of which are incorporated herein by reference in their entireties.

The invention is directed to a process to treat a carbon dioxide comprising gas wherein carbon dioxide is converted to methane in the presence of an electron charged packed bed comprising of a carrier and microorganisms under anaerobic conditions.

A journal article titled Granular Carbon-Based Electrodes as Cathodes in Methane-Producing Bioelectrochemical Systems, Dandan Liu, Marta Roca-Puigros, Florian Geppert, Leire Caizán-Juanarena, Susakul P. Na Ayudthaya, Cees Buisman and Annemiek ter Heijne, Frontiers in Bioengineering and Biotechnology, June 2018 |Volume 6, article 78 described a process where carbon dioxide is converted to methane in the presence of an electron charged packed bed comprising of activated carbon granules and a mixed culture microorganisms under anaerobic conditions. The $CO_2$ was supplied as a gas to an aqueous solution having a pH of 7.1. The biocathode consisting of the electron charged packed bed comprising of activated carbon granules and a mixed culture microorganisms was charged for 2 minutes alternating with no charging for 4 minutes. The reported "current to methane" efficiency was 55%. The reported overall energy efficiency was 25%.

Figure 1:
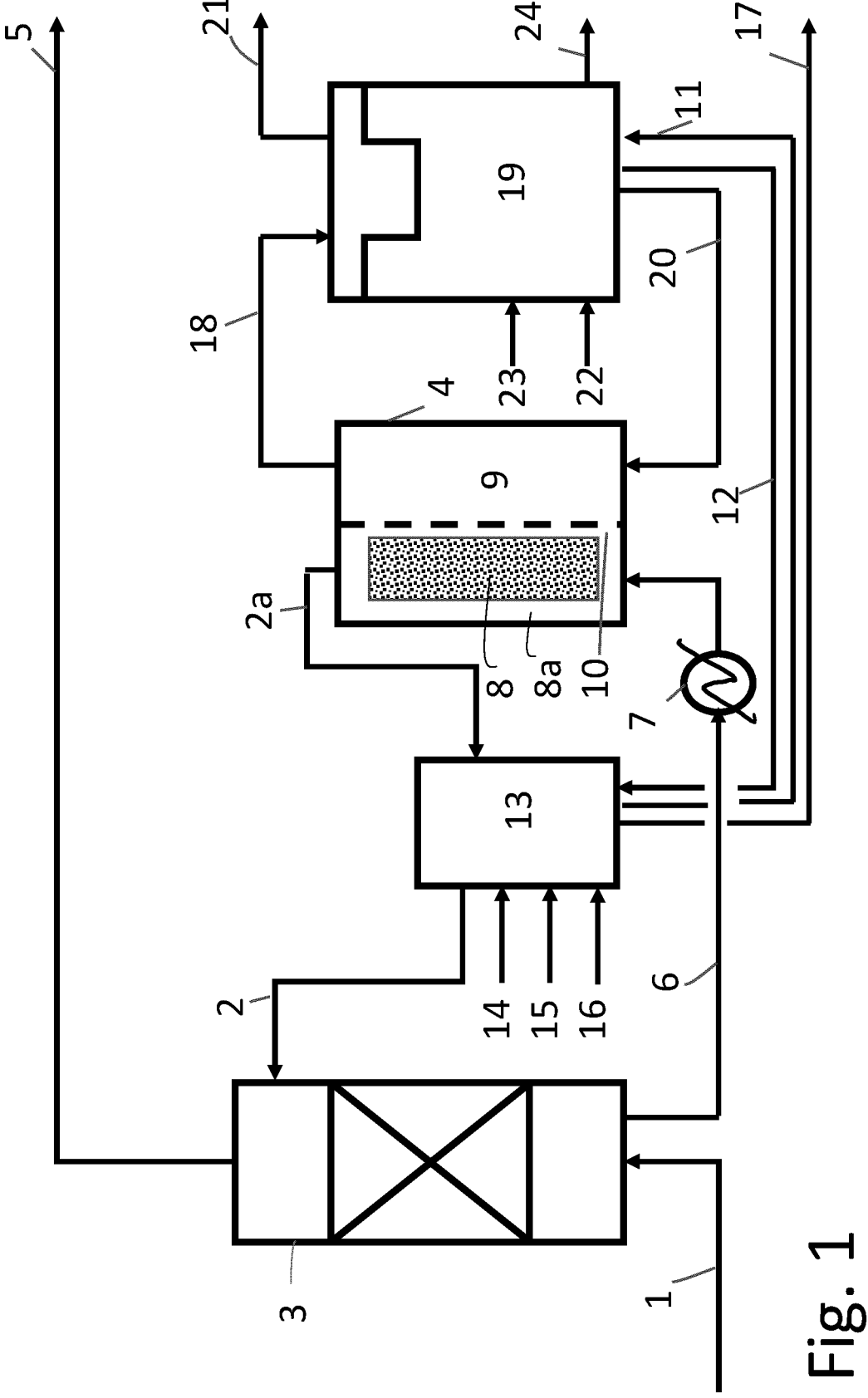
FIG. 1 shows a possible process scheme for the process of this invention.

It is an object of the present invention to improve the energy efficiency to produce methane.

This object is achieved by the following process.

A process to convert carbon dioxide to methane by contacting an aqueous solution comprising dissolved carbon dioxide with an electron charged packed bed comprising of a carrier and a biofilm of microorganisms under anaerobic conditions, wherein more than 90 mol % of the dissolved carbon dioxide in the aqueous solution is present as a bicarbonate ion and/or as a carbonate ion.

Applicants found that when the dissolved carbon dioxide is present as a bicarbonate ion and/or as a carbonate ion a significantly more energy efficient conversion to methane is achieved for the described process.

The dissolved carbon dioxide may be present as aqueous carbon dioxide, carbonic, bicarbonate ion and as a carbonate ions. A major part of the dissolved carbon dioxide in the aqueous solution is present as a bicarbonate ion and/or as a carbonate ion. More than 90 mol % and preferably more than 95 mol % of the dissolved carbon dioxide in the aqueous solution is present as a bicarbonate ion and/or as a carbonate ion. The pH conditions at which these compounds are present in an aqueous solution is preferably above 7.5, preferably above 7.7 and more preferably above 8 and even more preferably in the range of from 8 to 10, more preferably of from 8.5 to 9.5. These alkaline conditions may be achieved by a basic salt formed between a weak acid and a strong base, such as sodium bicarbonate and potassium bicarbonate. Such basic salt may be formed by adding sodium cations or sodium and potassium cations. The concentration of sodium cations or the total of sodium and potassium cations is suitably between 0.3 and 4 M, preferably between 0.4 and 2 M and even more preferred between 0.5 and 1.5 M. The resulting aqueous solution is a buffered solution further comprising sodium carbonate and sodium bicarbonate or potassium carbonate and potassium bicarbonate or their mixtures. The aqueous alkaline solution suitably further comprises nutrients for the microorganisms. Examples of suitable nutrients are nutrients such as ammonium, vitamin and mineral elements. It may be desired to add such nutrients to the aqueous alkaline solution in order to maintain active microorganisms.

The anaerobic conditions are suitably achieved by performing the process in the absence of molecular oxygen, preferably also in the absence of other oxidants such as for example nitrate. By 'in the absence of molecular oxygen' is meant that the concentration of molecular oxygen in the loaded aqueous solution in this process is at most 10 μM molecular oxygen, preferably at most 1 μM, more preferably at most 0.1 μM molecular oxygen. Sulfate, which may be regarded to be an oxidant, may be present at low concentrations of for example 160 μM, as part of a so-called Wolfe's mineral solution. It has been found that the sulfate at these low concentrations does not negatively influence the desired conversion of carbon dioxide.

The process is performed by contacting the aqueous solution with an electron charged packed bed comprising of activated carbon granules and microorganisms under anaerobic conditions wherein carbon dioxide is converted to methane. The microorganisms may be a mixed culture of microorganisms or a monoculture. The mixed culture of microorganisms is suitably obtained from an anaerobically grown culture. Suitably the mixed culture comprises hydrogenotrophic methanogens, such as for example *Methanobacterium*. Further microorganisms may be present, including anaerobic or facultative anaerobic bacteria, for example Proteobacteria, such as for example *Deltaproteobacteria* and *Betaproteobacteria*.

The mixed culture microorganisms is preferably obtained from an anaerobic system, such as an anaerobically grown culture. The mixed culture may therefore be obtained from the sludge of an anaerobic bioreactor, such as an anaerobic fermenter, for example one used for anaerobic chain elongation; an anaerobic digestion reactor, for example an upflow anaerobic sludge blanket reactor (UASB); Other suitable bioreactors for providing the sludge are expended granular sludge bed (EGSB), a sequential batch reactor (SBR), a continuously stirred tank reactor (CSTR) or an anaerobic membrane bioreactor (AnMBR). In the present context, the term sludge refers to the semi-solid flocs or granules containing a mixed culture of microorganisms.

The carrier may be any carrier which provides a surface for the biofilm and has a sufficient capacitance property. Preferably the carrier is biocompatible and has a 3D granular structure for attachment of the microorganisms and to enhance the mass transfer of the bulk solution and the electrode. Preferably the carrier is carbon based. Examples of suitable carbon based carriers are graphite and activated carbon granules.

The packed bed of the carrier suitably comprises of granules or particles of activated carbon or electrodes modified by activated carbon materials, such as by activated carbon powder granules or activated biochar granules. Suitably the bed is a packed bed of activated carbon granules having an activated surface area of between 500 and 1500 $m^2/g$ and wherein the microorganisms are present as a biofilm on the surface of the activated surface area. The high surface area provides a surface on which the microorganisms are present. A high surface area per volume thus provides a higher capacity to perform the desired reaction of carbon dioxide to methane per volume of reactor space.

The dimensions of the granules are suitably such that on the one hand a mass transport of the aqueous fractions is possible in the spaces between the granules without causing a high pressure drop. This means that there will be a practical lower limit with respect to the dimensions of the granules. On the other hand the granules should not be too large because this would result in long travel distances within the micropores of the activated carbon granules. The volume based diameter of the granules may be between 0.5 and 10 mm and preferably between 1 and 4 mm.

The electron charged packed bed comprising of activated carbon granules is preferably part of a biocathode in a bioelectrochemical system further comprising an anode. The biocathode suitably comprises a volume of activated carbon granules arranged in a packed bed. The packed bed contacts with a current collector, which may be a surface of a conductive electrode material, such as a carbon comprising materials such as a graphite plate or felt or a metal mesh, preferably a stainless steel mesh. The current collector is arranged such that the packed bed may be charged with electrons from said current collector.

The packed bed will further be positioned in a cathode space of the bioelectrochemical system which is fluidly connected to an anode space of the bioelectrochemical system and separated from said anode space by a cation exchange membrane. In order to compact the packed bed of activated carbon granules it may be preferred to add inert particles, like glass beads, to the anode space such to counter balance the pressure exercised by the packed bed on the cation exchange membrane.

The aqueous solution as present at the anode is referred to as the anolyte and the aqueous solution as present at the cathode is referred to as the catholyte. Suitably a recirculation is performed where part of the catholyte is fed to the anode to become part of the anolyte and part of the anolyte is fed to the cathode to become part of the catholyte. It is found that when such a recirculation is performed a more efficient process is obtained wherein the major part of the dissolved carbon dioxide in the aqueous solution is present as a bicarbonate ion and/or as a carbonate ion.

Preferably the content of oxygen as may be present in the anolyte should be low when this is fed to the cathode to become part of the catholyte. The oxygen content may be decreased by removing oxygen from this anolyte stream by means of a gas-liquid separation. Alternatively physical or chemical oxygen scavengers such as sulfite or an organic scavenger may be used to lower the oxygen content. Also the anolyte may be purged with $O_2$ free gasses, such as $N_2$ and/or $CO_2$. Oxygen may also be removed from the anolyte by electrochemical removal techniques.

Preferably the content of methane as may be present in the catholyte should be low when this is fed to the anode to become part of the anolyte. The methane content may be decreased by removing methane from this anolyte stream by means of a gas-liquid separation.

The packed bed of activated carbon granules may be charged in such a system by applying a potential to the bioelectrochemical system resulting in a current between biocathode and anode such that electrons are donated at the anode and at the cathode electrons are supplied to the packed bed. At the anode an oxidation reaction, such as water oxidation, takes place providing the required electrons. The potential may be achieved by an external power supply generating electricity, like for example power generated by wind and/or solar. Alternatively the electrons and thus the power supply may be partially donated by a chemical reaction at the anode. An example of such a chemical reaction is the biological organic matter (i.e. COD) oxidation as described in Cerrillo, M., Viñas, M. and Bonmati, A. (2017) Unravelling the active microbial community in a thermophilic anaerobic digester-microbial electrolysis cell coupled system under different conditions. Water Research 110, 192-201.

The anode will be placed in the anode space and may be made of a material suited for the oxidation of the chosen electron donor. Preferred materials for water as the electron donor are platinum, ruthenium, iridium, titanium coated with iridium and their mixtures. An example of a suitable anode material is a platinum-iridium-coated titanium plate. Preferably the anode is a iridium coated titanium mesh for example a ruthenium-iridium coated titanium mesh. It has been found that the electrochemically catalytic property for water oxidation of the iridium-tantalum coated titanium mesh is higher than the platinum-iridium-coated titanium anode. The experimental results have shown that the required anode potential for water splitting is much lower than in previous experiments: 1.14 V vs. Ag/AgCl (3M KCl) at a current density of 5 $A/m^2$ whereas previous experiments had 1.9 V vs. Ag/AgCl (3M KCl) at the same current density. It was expected that the anode potential would increase at an elevated current density of 10 $A/m^2$. However, the actual increase of the anode potential was negligible.

The charged packed bed is suitably charged to a capacitance of between 10 to 100 F/g. Preferably charging is performed in a bioelectrochemical system comprising a biocathode, an anode and a cation exchange membrane. The electron charged packed bed is part of the biocathode. The packed bed is charged by applying a voltage/current to the bioelectrochemical system resulting in a current between biocathode and anode for a certain time resulting in that the packed bed is loaded with electrons. Preferably the packed bed is charged by applying a cathode potential to the current collector of the biocathode of between −0.50 and −0.60V vs. Ag/AgCl, or by applying a current density to the cathode electrode of between 2 and 200 $A/m^2$ and preferably between 5 and 120 $A/m^2$.

The electron charged packed bed does not necessarily have to be connected to an external power supply such that no power is supplied when performing the process. When the packed bed is sufficiently charged with electrons it is found that the process performs for a prolonged period of time. For example the process may be performed for between 0.03 and 12 hours, preferably between 0.05 and 10 hours, in a situation wherein no power is supplied to the electron charged packed bed. This is advantageous because this allows the use of a non-continuous power supply generating electricity, preferably a sustainable and renewable external power supply, such as for example solar and/or wind. The capability of the process to operate when such a non-continuous power supply is temporally not available is advantageous.

The process may be performed using an electron charged packed bed as part of the above described bioelectrochemical system wherein no power is supplied to the electron charged packed bed of the bioelectrochemical system. In such an embodiment the packed bed is charged before performing the process as described above by applying a potential to the bioelectrochemical system resulting in a current between biocathode and anode. The process may also be performed when the packed bed is charged as described above. Also possible is that the process is performed wherein the packed bed is alternatingly charged and not charged because of the absence of an external power supply. In this embodiment some net charging will take place when performing the process. The system will then be connected to an external power supply to supply power.

The process may also be performed in more than one bioelectrochemical system, each system comprising of the biocathode and an anode, and wherein one bioelectrochemical system performs the process and another bio electrochemical system is charged. The system performing the process may be performed while no power is supplied to the electron charged packed bed. To the bioelectrochemical system which is charged power is supplied such that the packed bed is charged with electrons. Optionally a further bioelectrochemical system of the more than one bioelectrochemical system performs the process while the packed bed is charged by applying a potential/current to the bioelectrochemical system.

Suitably the packed bed comprising of carrier and a biofilm of microorganisms is obtained in an activation step. The activation step is performed at a pH greater than 8 and under anaerobic conditions and by supplying an amount of current at a cathode potential which is lower than the theoretical hydrogen evolution potential at −0.61 V vs Ag/AgCl (3M KCl) to the packed bed comprising of carrier and a biofilm of microorganisms from a sludge of an anaerobic wastewater treatment plant. It has been found that the resulting packed bed, especially comprising of activated carbon granules and a mixed culture microorganisms, is more robust and avoids hydrogen evolution at the cathode when compared to when such an activation does not take place. The activation is preferably performed until stable and optimal potential is obtained after turning on the current supply.

The invention is also directed to a method to activate or reactivate a bioelectrochemical system comprising of an anode and a biocathode comprising of packed bed comprising of a carrier and a mixed culture microorganisms from the sludge of an anaerobic wastewater treatment plant, by supplying an amount of current such that the cathode potential is lower than −0.61 V vs Ag/AgCl (3M KCl) under anaerobic conditions and at a pH of greater than 8. To avoid confusion the above method to activate or reactivate a bioelectrochemical system is performed by supplying a current at a cathode potential which is more positive than the theoretical hydrogen evolution potential at −0.61 V vs Ag/AgCl (3M KCl) at pH of 7. The theoretical hydrogen evolution potential is pH dependent. For example, at a pH of 5 the theoretical hydrogen evolution potential is −0.71 V vs Ag/AgCl (3M KCl).

The aqueous solution comprising dissolved carbon dioxide may be a solution purposely made or a natural occurring solution such as sea water. Purposely made aqueous solutions may be obtained by contacting a gas comprising carbon dioxide with an aqueous solution having a pH of above 8 to obtain an aqueous solution wherein a major part of the dissolved carbon dioxide is present as a bicarbonate ion and/or as a carbonate ion. The aqueous solution having a pH of above 8 in such an absorption process step suitably comprises sodium ions or sodium and potassium ions as described above. The carbon dioxide comprising gas may be any gas comprising carbon dioxide. Examples of such gasses are flue gases obtained in combustion processes, effluent gasses of a water gas shift process, synthesis gas, biogas from anaerobic digestion for wastewater treatment, air, amine acid gas, natural gas, associated gas, (bio) refinery gas, gas streams originating from gasification of biomass, coal or other organic residues.

The absorption process step is typically performed in an absorption or contacting column where gas and liquid flow counter-currently. Suitably the absorption process step is performed in a vertical column wherein continuously the carbon dioxide comprising gas is fed to the column at a lower position of the column and the aqueous alkaline solution is continuously fed to a higher position of the column such that a substantially upward flowing gaseous stream contacts a substantially downwards flowing liquid stream. The column is further provided with an outlet for the loaded aqueous solution at its lower end and an outlet for the gas having a lower content of carbon dioxide at its upper end.

The pH of the aqueous solution in the absorption process will decline as a result of the carbon dioxide which is dissolved. For this reason the pH of the starting aqueous solution and its composition should preferably be such that in the obtained liquid aqueous solution in the major part of the dissolved carbon dioxide is present as a bicarbonate ion and/or as a carbonate ion. Optionally alkaline compounds can be added after the absorption step to achieve these conditions.

The temperature in the absorption process step may be between 5 and 45° C. and preferably between 30 and 40° C. The pressure may be in the range of from 0 bara to 100 bara, preferably of from atmospheric pressure to 80 bara.

The absorption process step is preferably performed such that no oxygen is dissolved in the loaded aqueous solution. This may be achieved by starting with a carbon dioxide gas having a low oxygen content. If the gas however contains oxygen some pretreatment may be required. Traces of oxygen are allowed as traces of oxygen will also enter the cathode compartment via the membrane from the anode where oxygen is formed in one preferred embodiment.

Preferably the gas comprising carbon dioxide is counter currently contacted with an aqueous solution having a pH of above 8 and comprising dissolved methane as obtained in the process according to this invention and wherein the gas strips the methane from the aqueous solution to obtain a gas comprising methane. In this way methane is effectively isolated from the aqueous reaction mixture while carbon dioxide is absorbed using the same unit operation.

FIG. 1 shows a possible process scheme for the process of this invention. A gas comprising carbon dioxide (1) is counter currently contacted in absorption column (3) with an aqueous solution (2) having a pH of above 8 and comprising dissolved methane as obtained in reactor (4). In column (3) the gas (1) strips the methane from the aqueous solution (2) to obtain a gas comprising methane. In this way methane is effectively isolated from the aqueous reaction mixture (2,2a) while carbon dioxide is absorbed in the same column (3). The methane rich gas is obtained as gas stream (5). In the obtained aqueous solution (6) comprising dissolved carbon a major part of the dissolved carbon dioxide is present as a bicarbonate ion and/or as a carbonate ion. This aqueous solution (6) is cooled in heat exchanger (7) and fed to an electron charged packed bed (8) comprising of a carrier and a biofilm of microorganisms under anaerobic conditions. In the electron charged packed bed (8) carbon dioxide as the bicarbonate ion and/or as the carbonate ion reacts to methane. It is believed that this is achieved without the formation of hydrogen as an intermediate reaction product. The electron charged packed bed (8) is part of a biocathode (8a) in a bioelectrochemical reactor (4) further comprising an anode (9) and an ion exchange membrane (10) to avoid oxygen as may be formed at the anode (9) to flow to the biocathode (8a). The membrane is optional. In case that the reactor (4) is such designed that no methane produced at biocathode (8a) is ending up in anode (9) and no oxygen produced at anode (9) is ending up in biocathode (8a), no membrane is required.

The aqueous reaction mixture (2,2a) obtained at the biocathode (8a) is fed to column (3) via a mixture vessel (13). To mixture vessel (13) make up water (14), make up caustic (15) and make up nutrients and vitamins (16) may be added. A catholyte bleed stream (17) discharges part of the catholyte from the process.

At the anode water is oxidised and the oxygen as formed is discharged via (18) to an anolyte buffer vessel (19). The anolyte compartment of the reactor (9) is fed with fresh anolyte via (20). In this vessel molecular oxygen is separated as (21). Make up water (22) and make up caustic (23) is added and an anolyte bleed stream (24) discharges part of the aqueous solution from the process.

Part of the anolyte (12) is fed to the mixture vessel (13) to become part of the catholyte and part of the catholyte (11) is fed to the anolyte buffer vessel (19) to become part of the anolyte. These streams (11,12) may be treated to lower the content of oxygen and methane as described above.

The invention is illustrated by the following non-limiting examples. In these examples the energy efficiency of the process is shown. This energy efficiency is defined as follows. In general, the energy efficiency of an electron driven process as the process according to this invention is described as the external electrical energy that ends up in the aimed end-product methane. The energy efficiency is calculated as Equation 1.

$$\eta_{energy} = \eta_{product} \times \eta_{voltage} \qquad \text{(Eq. 1)}$$

For the $CH_4$ producing process of this invention, $\eta_{product}$ is the current-to-methane efficiency. This is described as the efficiency of capturing electrons from the electric current in the form of $CH_4$, which is calculated as shown in Equation 2.

$$\eta_{product} = \frac{N_{CH4} \times 8 \times F}{\int_{t=0}^{Idt} t} \qquad \text{(Eq. 2)}$$

Where $N_{CH4}$ is the amount of methane produced (in mole) during a certain amount of time (t); 8 is the amount of electrons required to produce 1 molecule of $CH_4$; F is the Faraday constant (96485 C/mol e⁻); I is the current (A).

The voltage efficiency ($\eta_{voltage}$) is described as the part of the energy input (i.e. the required cell voltage to run the system) which ends up in $CH_4$, which is calculated as shown in Equation3.

$$\eta_{voltage} = \frac{-\Delta G_{CH_4}}{E_{cell} \times 8 \times F} \qquad \text{(eq. 3)}$$

In this equation $\Delta G_{CH4}$ is the change in Gibb's free energy of oxidation of $CO_2$ to $CH_4$ ($890 \times 10^3$ J/mol $CH_4$); $E_{cell}$ is the applied cell voltage (V); 8 is the amount of electrons required to produce one molecule of $CH_4$; F is the Faraday constant (96485 C/mol e⁻).

EXAMPLE 1

A bioelectrochemical system (BES) was operated, for a 60-days long experiment. The BES setup is similar to the BES setup described in Liu, Dandan, Marta Roca-Puigros, Florian Geppert, Leire Caizán-Juanarena, Na Ayudthaya, P. Susakul, Cees Buisman, and Annemiek Ter Heijne. "Granular carbon-based electrodes as cathodes in methane-producing bioelectrochemical systems." Frontiers in bioengineering and biotechnology 6 (2018): 78. The cathode electrode was 10.3 g of granular activated carbon, which was fully packed in the cathodic chamber. A plain graphite plate was used as a current collector. An anodic chamber and a cathodic chamber with a flow channel of 33 cm³ each (11 cm×2 cm×1.5 cm). The anodic chamber and cathodic chamber were separated by a cation exchange membrane with a projected surface area of 22 cm² (11 cm×2 cm). The total volume of anolyte and catholyte were 500 mL and 330 mL, respectively. The catholyte circulation bottle was designed such that the H/D (height/diameter) ratio was increased to enable a better absorption of $CO_2$. In order to remove $O_2$ produced at the anode electrode, a high anolyte flow rate of 94 mL/min was used. Also, $N_2$ was continuously bubbled at the rate of 80 mL/min in the anolyte recirculation bottle. The catholyte recirculation rate was 11 mL/min.

The cathodic chamber was inoculated with 30 mL of anaerobic sludge from an upflow anaerobic sludge blanket (UASB) digestion in Eerbeek. The volatile suspended solids of the inoculated anaerobic sludge was 30.6 g/L. The methane-producing BES was galvanostatically controlled (fixed current) by a potentiostat. In addition, cell voltage was manually monitored via a multimeter. Liquid samples for pH and conductivity measurements were taken twice per week for both anolyte and catholyte. The following results were obtained.

Initially, the catholyte consisted of a 50 mM phosphate buffer (1.36 g/L $KH_2PO_4$ and 5.67 g/L $Na_2HPO_4$) with 0.2 g/L $NH_4Cl$, 1 mL/L Wolfe's vitamin solution and 1 mL/L Wolfe's modified mineral solution. The anolyte consisted only of the 50 mM phosphate buffer. Due to the use of the same phosphate buffer for both catholyte and anolyte, the initial pH and conductivity of catholyte and anolyte are the same (i.e. a pH of 6.7 and a conductivity of 7.68 mS/cm). After a start-up period (not shown), stable performance was obtained (day 0-day 30) when providing electrons at the biocathode with a current density of 5 A/m². In this period, the obtained voltage efficiency was about 50% and the coulombic efficiency and a coulombic efficiency of 83-85% which leads to an energy efficiency of 40-42%.

Figure 2:
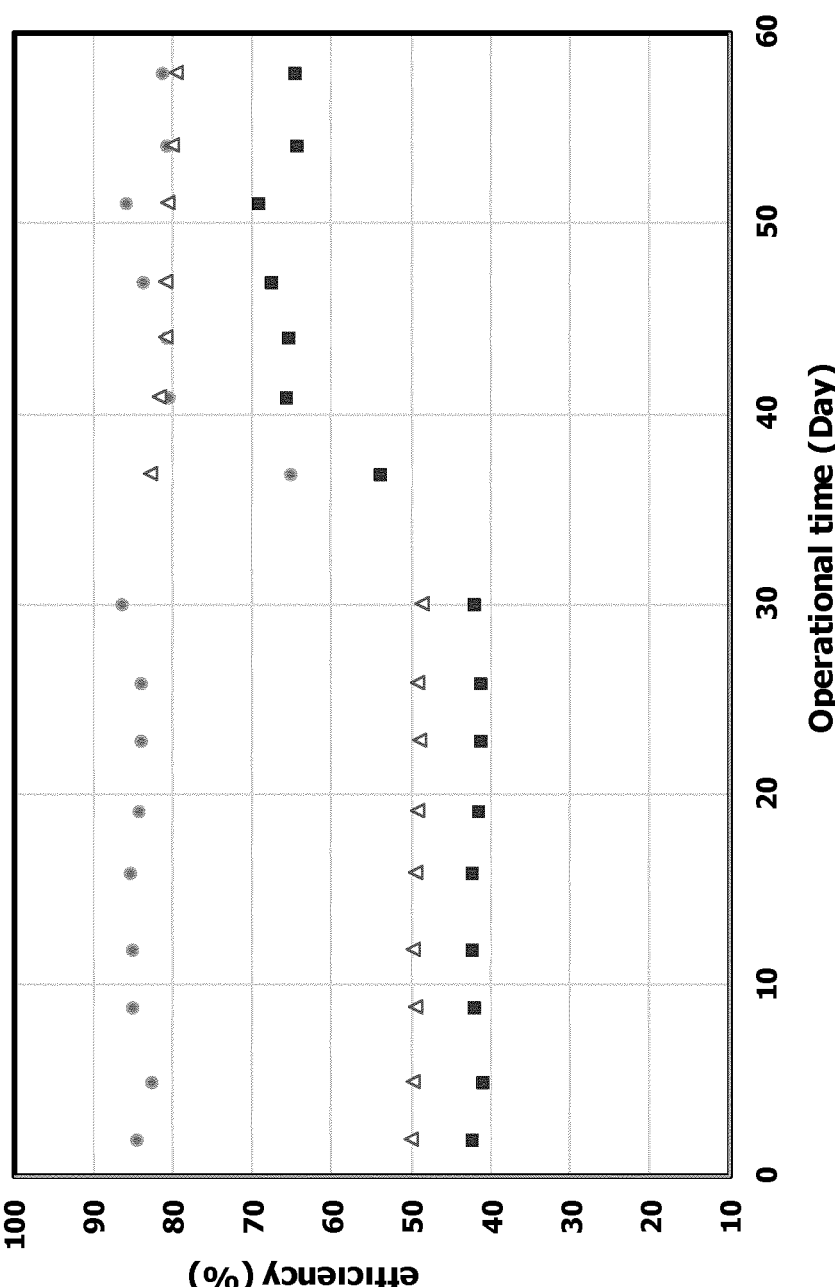
FIG. 2 shows the Coulombic efficiency, voltage efficiency and energy efficiency results of Example 1.

After 30 days, the catholyte and anolyte were changed to a high saline medium, containing 1.0 M carbonate/bicarbonate buffer with a conductivity of around 40 mS/cm (Na:K of 4:1). The medium contained 0.2 g/L $NH_4Cl$, 1 mL/L Wolfe's vitamin solution and 1 mL/L Wolfe's modified mineral solution. The resulting pH of the catholyte was 7.7-7.8. After the change of medium, voltage efficiency immediately increased to ~83%. Coulombic efficiency initially dropped to 65%. This drop can be explained by a osmotic shock to the biocathode. However, after a few days of operation, the biofilm adapted and coulombic efficiency recovered to about 85%. As a result, due to the change in medium, the energy efficiency, $\eta_{energy}$, of the methane-producing BES increased from 43% towards 65-70%. See also FIG. 2 where the Coulombic efficiency is represented by the circles, the voltage efficiency by the open triangles and the energy efficiency by the closed squares.

The invention claimed is:

1. A process to convert carbon dioxide to methane by contacting an aqueous solution comprising dissolved carbon dioxide with an electron charged packed bed comprising of a carrier and a biofilm of microorganisms under anaerobic conditions, wherein the aqueous solution comprises:

a) between 0.3 and 4 M sodium cations, or b) between 0.3 and 4 M sodium and potassium cations, such that more than 90 mol % of the dissolved carbon dioxide in the aqueous solution is present as a bicarbonate ion and/or as a carbonate ion.

2. The process according to claim 1, wherein the carrier is activated carbon granules or activated biochar granules.

3. The process according to claim 1, wherein no power is supplied to the electron charged packed bed.

4. The process according to claim 3, wherein the electron charged packed bed is part of a biocathode in a bioelectrochemical system further comprising an anode, an ion exchange membrane, and a cathode;

wherein the packed bed is charged by applying a potential to the bioelectrochemical system resulting in a current between biocathode and anode for a certain time.

5. The process according to claim 4, wherein the aqueous solution as present at the anode is referred to as the anolyte and the aqueous solution as present at the cathode is referred to as the catholyte and wherein a recirculation is performed where part of the catholyte is fed to the anode to become part of the anolyte and part of the anolyte is fed to the cathode to become part of the catholyte.

6. The process according to claim 4, wherein the process is performed in more than one bioelectrochemical systems, each system comprising of the biocathode and an anode; and wherein in one or more bioelectrochemical systems the process is performed while no power is supplied to the electron charged packed bed of these one or more bioelectrochemical systems; and wherein power is supplied to the packed bed of one or more other bioelectrochemical system of the more than one bioelectrochemical systems such that these packed beds are charged with electrons while the process is not performed.

7. The process according to claim 4, wherein the packed bed is charged by applying a cathode potential to the cathode electrode of between −0.50 and −0.60V vs. Ag/AgCl (3M KCl) or by applying a current density to the cathode electrode of between 5 and 200 A/m².

8. The process according to claim 4, wherein the anode is a titanium mesh coated with iridium and/or tantalum.

9. The process according to claim 4, wherein the power supply is generated by a chemical reaction at the anode.

10. The process according to claim 4, wherein the carrier and a biofilm of microorganisms is obtained in an activation step which activation step is performed at a pH greater than 8 and under anaerobic conditions and by supplying an amount of current at a cathode potential which is more positive than the theoretical hydrogen evolution potential at −0.61 V vs Ag/AgCl (3M KCl) at a pH of 7 to the packed bed comprising of carrier and biofilm of microorganisms; and wherein the microorganisms are a mixed culture microorganisms from a sludge of an anaerobic wastewater treatment plant.

11. The process according to claim 1, wherein the electron charged packed bed is part of a biocathode in a bioelectrochemical system further comprising an anode; and wherein at one moment in time the process is performed when the packed bed is charged by applying a potential to the bioelectrochemical system resulting in a current between biocathode and anode; and wherein at another moment in time the process is performed when no power is supplied to the electron charged packed bed.

12. The process according to claim 11, wherein the process is performed for between 0.03 and 12 hours when no power is supplied to the electron charged packed.

13. The process according to claim 11, wherein the power supply is electricity generated by solar and/or wind.

14. The process according to claim 1, wherein the packed bed is a packed bed of activated carbon granules having an activated surface area of between 500 and 1500 m²/g; and wherein the microorganisms are present as a biofilm on the surface of the activated surface area.

15. The process according to claim 1, wherein the pH of the aqueous solution is above 7.7.

16. The process according to claim 15, wherein the pH of the aqueous solution is above 8.

17. The process according to claim 1, wherein the aqueous solution comprises between 0.5 and 1.5 M sodium cations or between 0.5 and 1.5 M sodium and potassium cations.

18. The process according to claim 1, wherein the aqueous solution comprising dissolved carbon dioxide is obtained by contacting a gas comprising carbon dioxide with an aqueous solution having a pH of above 8 to obtain an aqueous solution wherein a major part of the dissolved carbon dioxide is present as a bicarbonate ion and/or as a carbonate ion.

19. The process according to claim 18, wherein the gas comprising carbon dioxide is counter currently contacted with the aqueous solution having a pH of above 8 and comprising dissolved methane as obtained a process comprising:

contacting an aqueous solution comprising dissolved carbon dioxide with an electron charged packed bed comprising of a carrier and a biofilm of microorganisms under anaerobic conditions, wherein more than 90 mol % of the dissolved carbon dioxide in the aqueous solution is present as a bicarbonate ion and/or as a carbonate ion; and wherein the gas strips the methane from the aqueous solution to obtain a gas comprising methane.

*     *     *     *     *